United States Patent [19]

Denicola et al.

[11] Patent Number: 4,688,270
[45] Date of Patent: Aug. 25, 1987

[54] GARMENT FOR SHIELDING LINES CONNECTED TO A PATIENT DURING INVASIVE THERAPY

[75] Inventors: Patricia J. Denicola, Cincinnati; Patricia A. Gorgone, West Chester, both of Ohio

[73] Assignee: Children's Hospital Medical Center, Cincinnati, Ohio

[21] Appl. No.: 935,749
[22] Filed: Nov. 28, 1986
[51] Int. Cl.$^4$ .................... A61F 13/00; A41B 1/12
[52] U.S. Cl. ........................... 2/102; 128/134; 2/69.5
[58] Field of Search ............. 2/69.5, 69, 102, 46, 2/73; 128/132, 133, 134

[56] References Cited

U.S. PATENT DOCUMENTS

| | | |
|---|---|---|
| 1,573,446 | 2/1926 | Popham . |
| 1,709,204 | 4/1929 | Certia . |
| 1,808,496 | 6/1931 | Dillon . |
| 1,964,271 | 6/1934 | O'Dwyer . |
| 2,034,954 | 3/1936 | Murphy . |
| 2,140,797 | 12/1938 | Hammerman . |
| 2,194,123 | 3/1940 | Neil . |
| 2,316,602 | 4/1943 | Lee . |
| 2,328,938 | 9/1943 | Wilson . |
| 2,342,069 | 2/1944 | Wilkinson . |
| 2,362,465 | 11/1944 | Carner . |
| 2,374,712 | 5/1945 | Steigerwald . |
| 2,401,026 | 5/1946 | Steigerwald . |
| 2,423,392 | 7/1947 | Krogh . |
| 2,429,168 | 10/1947 | Padgett ............................ 2/69.5 |
| 2,455,884 | 12/1948 | Steigerwald . |
| 2,521,175 | 9/1950 | Kruse . |
| 2,524,429 | 10/1950 | Devin . |
| 2,530,606 | 11/1950 | Farrington . |
| 2,531,716 | 11/1950 | Wolf . |
| 2,535,936 | 12/1950 | Langley . |
| 2,536,363 | 1/1951 | Godbout . |
| 2,566,046 | 8/1951 | Weinstein . |
| 2,578,323 | 12/1951 | Sillaway . |
| 2,586,961 | 3/1952 | Klein . |
| 2,589,708 | 3/1952 | Koster . |
| 2,594,883 | 4/1952 | Donnen . |
| 2,657,688 | 11/1953 | Tucker . |
| 2,675,557 | 4/1954 | Kempner, Jr. . |
| 2,751,594 | 6/1956 | Brissenden . |
| 2,758,595 | 8/1956 | Lovett . |
| 2,827,048 | 3/1958 | Lupien . |
| 2,888,009 | 5/1959 | Taylor . |
| 3,230,546 | 1/1966 | Sabee . |
| 3,236,234 | 3/1966 | Buckley . |
| 3,259,126 | 7/1966 | Greiert . |
| 3,265,065 | 8/1966 | Jillson . |
| 3,276,430 | 10/1966 | Murcott . |
| 3,315,671 | 4/1967 | Creelman . |
| 3,407,807 | 10/1968 | Giberson . |
| 3,526,222 | 9/1970 | Dreibelbis . |
| 3,536,067 | 10/1970 | Sternagel . |
| 3,566,864 | 3/1971 | Garrow . |
| 3,606,885 | 9/1971 | Lund . |
| 3,633,215 | 1/1972 | Richards . |
| 3,641,997 | 2/1972 | Posey, Jr. . |
| 3,742,945 | 7/1973 | Reinhardt . |
| 3,788,309 | 1/1974 | Zeilman . |
| 3,920,012 | 11/1975 | Patel . |
| 4,117,840 | 10/1978 | Rasure . |
| 4,119,095 | 10/1978 | Lewis . |
| 4,132,230 | 1/1979 | Ladd . |
| 4,360,014 | 11/1982 | Manahan ..................... 128/134 |
| 4,471,767 | 9/1984 | Guimond . |
| 4,488,544 | 12/1984 | Triunfol . |

Primary Examiner—Doris L. Troutman
Attorney, Agent, or Firm—Wood, Herron & Evans

[57] ABSTRACT

A garment for shielding from an infant's head and hands intravenous and gastrostomy lines infused into the infant during invasive therapy. The garment accomplishes its shielding objectives without restraining the infant's head or limbs while promoting mental health and development through free movement and play. The garment generally speaking is a sleeveless wrap-around type vest provided with a clotch tab attached to the interior side of the front of the vest for anchoring a portion of the infused line located underneath the vest when it is positioned on the infant. The vest is also uniquely provided with an opening for permitting portions of the infused line to exit from beneath the vest and with cooperating components attached to the exterior side of the vest for further anchoring portions of the infused line which have exited from beneath the vest via the opening. Since the vest is of the wrap-around type, it conforms comfortably to the torso of the infant, shields the infused lines from the infant's head and limbs and encourages the infant to engage in free movement and play.

20 Claims, 4 Drawing Figures

GARMENT FOR SHIELDING LINES CONNECTED TO A PATIENT DURING INVASIVE THERAPY

FIELD OF THE INVENTION

The present invention relates to garments, and more particularly relates to wrap-around vest-like garments for shielding lines connected to a patient during invasive therapy.

BACKGROUND

Intravenous and gavage therapy are often prescribed in hospitals for infants diagnosed with serious illnesses. In the former procedure, a tunneled central catheter, which is connected to a volumetric pump and a bottle or bag via an intravenous line or tubing, is infused into an infant's superior vena cava or subclavial vein for delivering into the infant various pharmaceutical fluids via the infused line or tubing. This type of invasive therapy generally includes, inter alia, hyperalimentation, hydration and antimicrobial therapy. In the latter procedure, a gastrostomy tube is inserted into an infant's stomach via the skin for feeding of the infant through the tubing. Due to the foreign nature and placement of the line infused into the infant, the infant may intentionally or inadvertently disconnect the line with his hands or mouth by pulling on, splitting or biting it.

In the past, in order to prevent infants from dislodging infused lines, the infants' limbs were manually or mechanically restrained in some manner. When the infants' limbs were restrained manually, this proved to be inconvenient to the attendants administering or monitoring the invasive therapy. This also would sometimes interfere with and delay the administration of emergency care vitally needed by critically ill infants. When the infants' limbs were restrained mechanically, this was accomplished by, for instance, taping their hands to objects, such as mattresses, which proved to be restrictive and uncomfortable to the infants. Mechanical restraint was also accomplished by mechanical restraining devices, as exemplified in U.S. Pat. No. 3,920,012, which prevented free movement of the infants' arms. Regardless of whether the infants were restrained manually or mechanically, such restraints in both cases prevented the infants from engaging in free movement, interferred with mental health and development and discouraged play.

In view of the disadvantages associated with present methods and devices for preventing infants from removing or dislodging intentionally or inadvertently infused lines associated with invasive therapy, there is a definite need to develop means which prevent infants from removing or dislodging such infused lines without interferring with the infants' free movement or play, which are comfortable to the infants, which do not inconvenience attendants administering or monitoring the invasive therapy and which do not interfere with or delay the administration of such therapy.

SUMMARY OF THE INVENTION

In brief, the present invention alleviates the above mentioned problems and shortcomings of the present state of the art through the discovery of a novel pediatric garment designed to protect lines infused into an infant during invasive therapy while promoting mental health and development of the infant through his unrestricted movement and play. More particularly, the pediatric garment is preferably a sleeveless wrap-around type vest which conforms to the torso of the infant's body while shielding the infused lines from the infant's hands and mouth. This unique feature of shielding is amazingly accomplished without restricting or restraining the head or limbs of the infant so that the infant is free to engage in unrestricted movement and play throughout invasive therapy. Moreover, the pediatric garment is easily fitted to the infant so that the inconvenience caused to the attendants administering or monitoring the invasive therapy and the interference or delay previously associated with the administration of such therapy is minimized.

In one embodiment, the garment is preferably a sleeveless wrap-around type vest having wide sleeve and leg openings and adjustable crotch ties to allow for variance in patient heights. The vest comprises a back panel and two front panels designed to attach at the front of the patient in an overlapping position. In one important feature, the vest is designed with a high neckline which preferably comprises a neck encircling edge that is positioned immediately adjacent to the patient's neck to shield the lines infused underneath the vest from the patient's head and hands. In another important feature, a flap or Velcro ® components are located on the interior side of a front panel which is adapted to receive and anchor the infused intravenous and gastrointestinal lines thereto. In another important feature, the side seams positioned between the front and back panels provide for an opening at the waist to permit portions of the anchored infused lines to exit from beneath the vest. In still another important feature, anchoring tabs, such as Velcro ® components, are located on the exterior side of the back panel which are designed to support the weight of the lines and receive portions of the exiting infused lines to support the weight of the lines and to prevent the patient from intentionally or inadvertently dislodging the infused lines.

In accordance with a further feature contemplated by the present invention, the garments are preferably made from soft fabric materials that are provided with colorful patterns which can be laundered routinely for repeated use. As a matter of comfort and to prolong the usable life of such garments, it is preferred to bind all seams and especially the interior seams generated in making the garments to prevent skin irritation and to avoid fraying of the fabric. As an additional feature, the basic design or pattern of the garments can be reversed, and they can be made in various sizes, such as small, medium, large, extra-large and so on, to accommodate size differences between patients.

Also contemplated by the present invention is that the garments may be used with patients other than infants such as geriatric patients as well as other patients requiring invasive type therapy. Of course, it should be well appreciated that the invasive therapy does not have to be limited to intravenous or gavage therapy, but may also include ostomy, gastrostomy and jejunostomy therapy to name a few.

The above features and advantages of the present invention will be better understood with reference to the accompanying Figs., Detailed Description and Example. It will also be understood that the particular garments illustrating the invention are exemplary only and not to be regarded as limitations of the invention.

BRIEF DESCRIPTION OF THE FIGS.

Reference is made to the accompanying Figs. in which is shown illustrative embodiments of the present invention from which its novel features and advantages will be apparent:

DETAILED DESCRIPTION OF THE INVENTION

Figure 1:
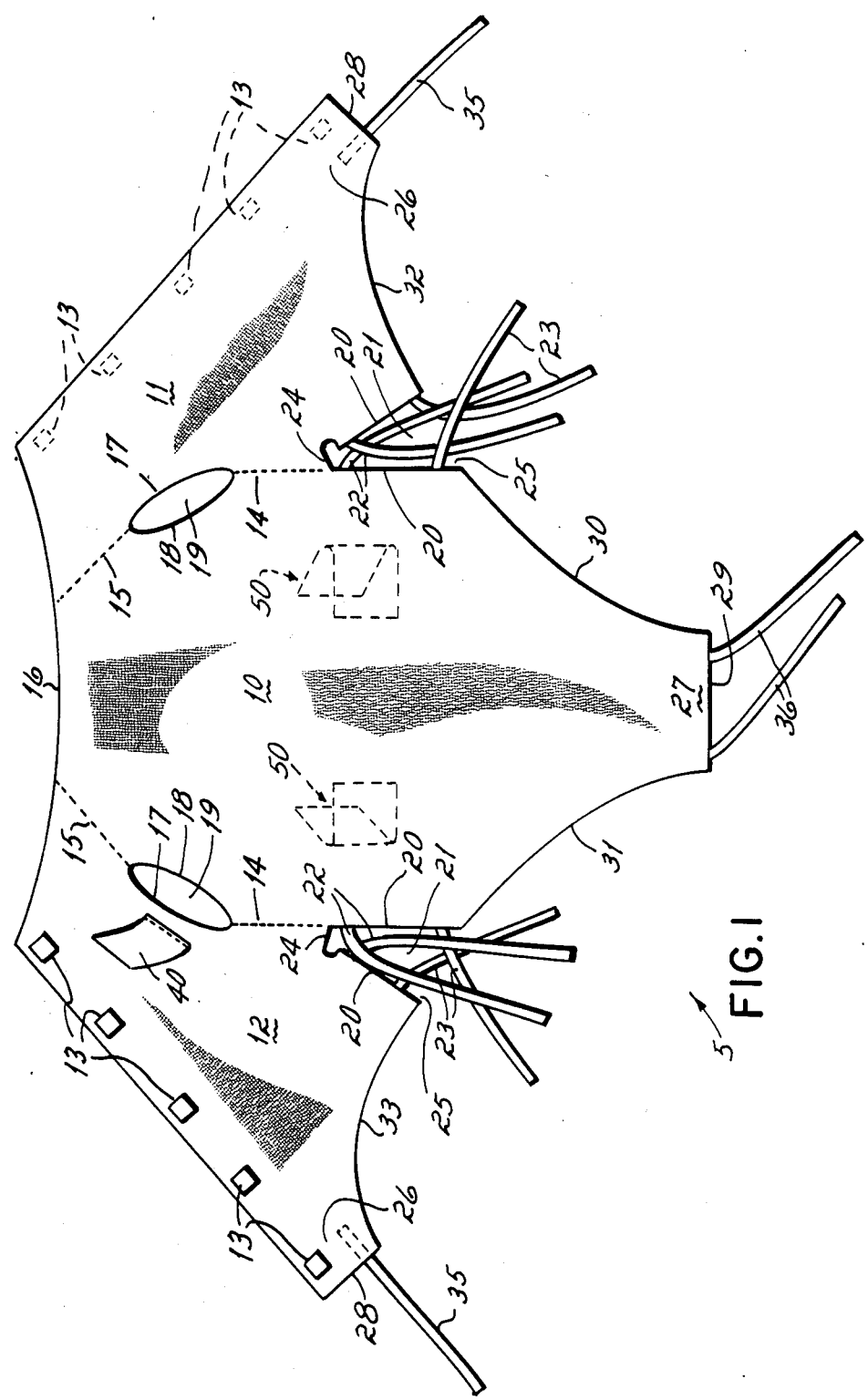
FIG. 1 is a plan view of a garment of the present invention as viewed from the interior.

By way of illustrating and providing a more complete appreciation of the present invention and many of the attendant advantages thereof, the following detailed description is given concerning the novel pediatric garment and methods of use thereof.

Referring now more particularly to the Figs. in which like reference characters indicate like elements throughout, the garment or vest generally speaking, is of the wrap-around type preferably constructed from those fabric materials that are soft, comfortable and easily washable for repeated use. Although preferable types of fabric materials that may be used to formulate the garments of the present invention include cotton, flannel, polyester and blends of cotton and polyester, any fabric material that meets the objectives of this invention may be used. Regardless of the type of fabric material selected, however, it is highly desirable to select those fabric materials provided with colorful patterns particularly when the fabric materials are for garments sized for use with infants.

As used herein, the term "invasive therapy" refers broadly to any therapy in which a line is connected to, that is, infused into or placed on, a patient for, inter alia, delivering a fluid into, draining a fluid or substance from, or monitoring a condition of the patient. By the term "line," it refers broadly to any object that may be connected to a patient for conducting invasive therapy. Exemplary of such lines that may be connected to a patient include intravenous lines or tubing, gastrointestinal tubes or catheters, gastrostomy, ostomy and jejunostomy devices and electrograph and electrocardiograph lines. For illustrative purposes, an ostomy device indicated at 38 is shown in FIG. 2, a gastrostomy device 42 having a gastrointestinal line 39 extending therefrom is depicted in FIGS. 2–4, and a tunneled central catheter 41 infused into the infant and having an intravenous line 37 extending therefrom is illustrated in FIGS. 2–4.

Figure 2:
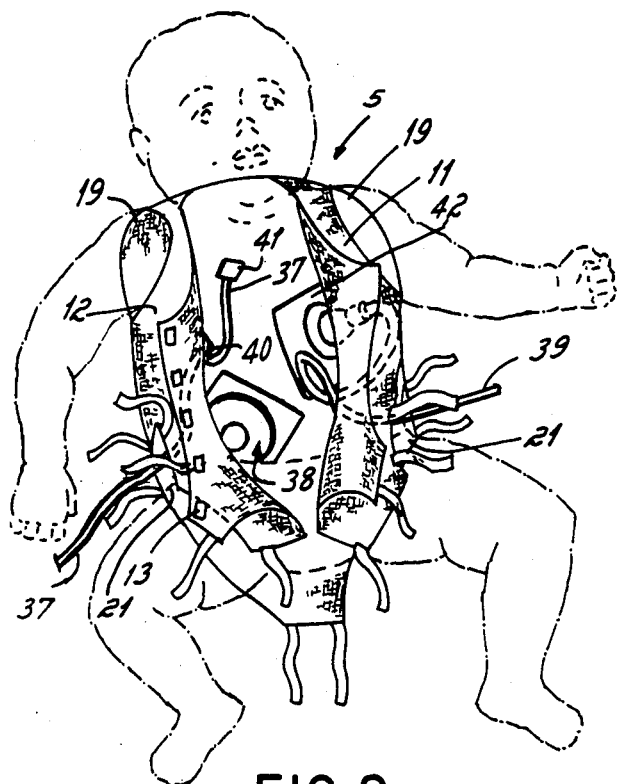
FIG. 2 is a view of a garment of the present invention positioned on an infant.
Figure 3:
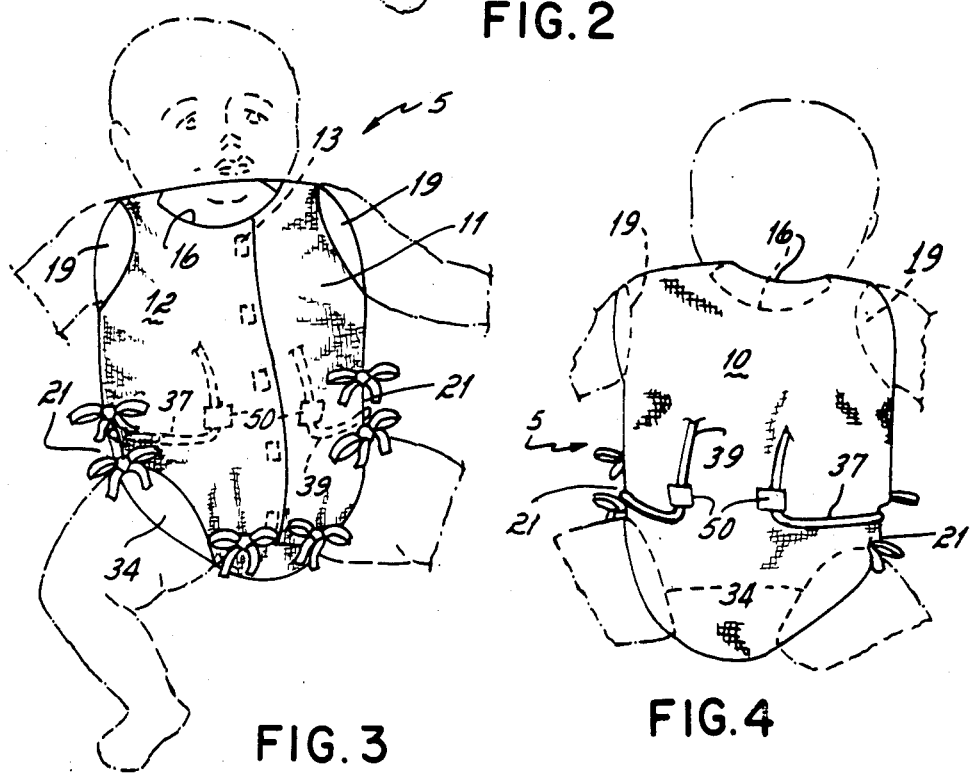
FIG. 3 is a front view of a garment of the present invention as it appears when fitted and tied securely to an infant.
Figure 4:
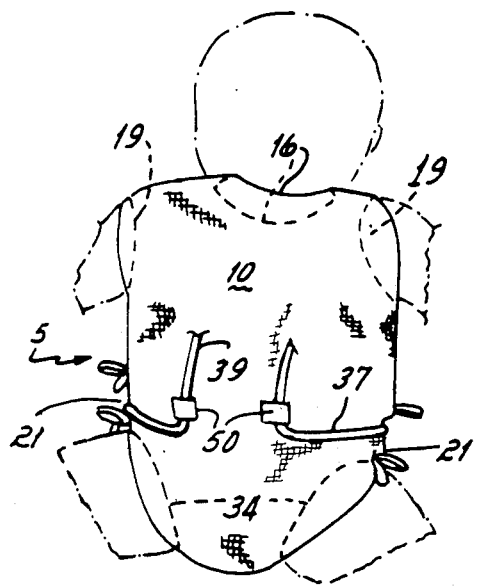
FIG. 4 is a rear view thereof.

The garment or vest, indicated generally at 5 and as illustrated in the Figs., and in FIG. 1 in particular, comprises a back panel 10 and a pair of oppositely opposed front panels 11 and 12 which are adapted to be attached at the front of the infant in an overlapping position, as shown in FIGS. 2 and 3. The front panels 11 and 12 may be joined together via tabs 13 constructed from cooperating components, such as velcro components which are sold under the trademark Velcro, as well as other attaching devices such as snaps, buttons, ties or the like. When Velcro ® components are employed, they comprise a loop pile component positioned on one front panel and a corresponding hook mutliple component positioned on the other front panel, as illustrated in FIG. 1. Front panels 11 and 12 are secured to back panel 10 along side seams 14 and shoulder seams 15. The upper edges of each front panel 11 and 12 and back panel 10 are curved to compliment and mate with one another to form the neck encircling part 16 of garment 5. It should be understood that the neck encircling part 16, otherwise referred to as the neckline, is entirely a matter of taste. However, a high neckline positioned immediately adjacent to the infant's neck, as can be viewed in FIGS. 2–4, is most preferred since front panels 11 and 12 of garment 5 act as shields for protecting the lines infused into the patient therebeneath.

Between side and shoulder seams 14 and 15, respectively, edges 18 of back panel 10 and edges 17 of each front panel 11 and 12 are curved to form arm-holes 19. Below side seams 14, each of the front panels 11 and 12 and back panel 10 are provided with unseamed or slit edges 20 to form side openings 21 at the waist for permitting the lines infused into the infant located beneath garment 5 to exit therethrough. Side openings 21 at the waist can be viewed in FIGS. 1–4. Oppositely opposed waist ties 22 and 23 are positioned at the top portions 24 and bottom portions 25, respectively, of slit edges 20 to permit side openings 21 at the waist to be opened and closed and to support the weight of the lines exiting therethrough. Although any suitable means can be used to close side openings 21, it is preferred to use cloth ties since they provide an access advantage, that is, in case of emergencies the cloth ties can be cut so that the infused lines underneath the vest can be accessed quickly. Cloth ties also provide the advantage of being relatively inexpensive to replace if it is necessary to cut them in emergency situations thereby preserving the vest for further use.

Both front panels 11 and 12 and back panel 10 are provided with crotch portions 26 and 27, respectively. The crotch portions 26 of front panels 11 and 12 and crotch portion 27 of back panel 10 are provided with tail edges 28 and 29, respectively. Opposite crotch edges 30 and 31 of back panel 10, which are positioned between bottom portions 25 of slit edges 20 and tail edge 29, are disposed in downwardly divergent relation to form, when positioned on an infant, leg-openings 34, as shown in FIG. 4. And, opposite crotch edges 32 and 33 of front panels 11 and 12, which are also positioned between bottom portions 25 of slit edges 20 and tail edges 28, are formed to a similar contour to also form, when positioned on an infant, leg openings 34, as shown in FIG. 3. Opposite crotch edges 30 and 31 of back panel 10 are disposed on a similar curvature as at 30 and 31, but oppositely disposed from crotch edges 32 and 33 of front panels 11 and 12 so that crotch portions 26 and 27 will fit snuggly around the legs and crotch of an infant via leg openings 34; the four crotch edges 30 and 32 and 31 and 33 form oppositely disposed parabolic-like cutout portions which can be observed in FIGS. 1, 3 and 4 and in FIG. 1 in particular. Adjustable ties 35 and 36 are located opposite each other on each tail edge 28 and 29 of front and back panels 11 and 12 and 10, respectively, to accommodate infant height variation so that crotch portions 26 and 27 can be securely connected to one another during use.

Attached onto the interior side of at least one front panel 11 or 12 of garment 5 is an anchoring device 40, such as a cloth tab sewn thereto, for anchoring lines infused into the infant which are located beneath garment 5, as illustrated in FIG. 1. Of course, it should be appreciated that one or more anchoring devices 40 may be attached to each or both front panels 11 and 12 if desired or necessary. Preferably, the anchoring device 40 is formed from a piece of fabric material and located in the interior upper quadrant of either or both front panels 11 and 12. Nonetheless, anchoring device 40 may comprise other materials, such as Velcro components, ties, snaps or the like, and be integrally secured to the interior sides of either or both front and back panels at any effective location. In use, anchoring device 40 enables attendants to secure the loose infused lines thereto, for example, via safety pins when anchoring device 40 is a cloth tab, to minimize the movement of the infused lines following their securement to the garment fitted on the infant. This is exemplified in FIG. 2 wherein intravenous line 37 extending from infused tunneled central catheter 41 is secured to anchoring device 40.

Likewise, integrally secured to the exterior side of back panel 10 are anchoring components 50, such as, cooperating components manufactured under the trademark Velcro ® as shown in FIG. 1, cloth tabs, ties, snaps or the like, for anchoring infused lines extending from underneath garment 5 and exiting from side opening 21 about the waist and for supporting the weight of such lines. The strategic location of such anchoring components 50 provides the attendant with the opportunity to secure the infused lines extending from underneath garment 5 and exiting through side opening 21 to the exterior portion of back panel 10 of garment 5 out of reach of the infant's hands and mouth. In addition, anchoring components 50 help to prevent an infant from tangling his legs and feet with infused lines which have exited from underneath the fitted garment. This is exemplified in FIG. 4 wherein exiting intravenous line 37 and gastrointestinal line 39 are secured to anchoring components 50.

Remarkably, the garment of the present invention accomplishes the shielding of the infused lines without restricting or restraining the infant's head or limbs. Thus, it should now be apparent to those versed in this area of art that the garment of the present invention is capable of promoting mental health and development through unrestricted movement and play while protecting the lines connected to the infant during invasive therapy.

To fit the infant with garment 5 of the present invention, the infant may be first placed in a sitting position. If an infant is too ill to sit, it is found to be more effective to fit the infant with the garment while he is maintained at all times in a supine position. While the infant is sitting, one arm is inserted through arm-hole 19. The lines connected to the infant can then be anchored to the interior anchoring device 40. With reference to FIG. 2, it illustrates intravenous line 37 anchored to the interior anchoring device 40. If anchoring device 40 is a cloth tab, as shown in FIG. 1, the connected lines can be pinned thereto via safety pins. If the connected lines are pinned, tape should be placed around the connected lines and pins as a safety measure and to further secure the connected lines to the interior anchoring device 40. After taping the connected lines and pins, the other arm of the infant can be slipped through the second arm-hole 19 permitting front panels 11 and 12 of garment 5 to be fitted to the infant and attached at the front of the infant in an overlapping position via the anchoring device 40 which can be viewed in FIG. 3. The infant can then be placed in a supine position so that the excess portions of the connected lines underneath the garment can be positioned in side opening 21 at the waist adjacent slit edges 20 and exited therefrom. The crotch ties 35 and 36 should be secured to fit garment 5 snuggly yet comfortably to the infant which is also shown in FIG. 3. Once the crotch ties have been secured, the attendant can then easily anchor the connected lines exiting side opening 21 by turning the infant onto it's side opposite the exiting connected lines and pulling the connected lines substantially taunt to secure the connected lines to back panel 10 of garment 5 via anchoring components 50. As can be seen in FIG. 4, it depicts intravenous line 37 and gastrointestinal line 39 being anchored to the exterior anchoring component 50. The infant is then placed back in a supine position in which waist ties 22 and 23 can be secured to close side openings 21, as illustrated in FIG. 4, and the infant can now engage in free movement and play. This is done without restraining or restricting the head or limbs of the infant and without fear that the infant will intentionally or inadvertently detach the connected lines by pulling on, splitting or biting them. It of course should be appreciated that the above describe procedure for fitting a garment of this invention to an infant is exemplary only and that any other suitable dressing procedure may be employed.

While it is preferred to construct the garments of this invention such that they conform to an infant's torso, it should be understood that the garments should be designed with enough depth to accomodate the lines connected to the infants therebeneath.

An example of the efficiency and effectiveness of the garment in accordance with the present invention will now be further illustrated with reference to the following Example.

EXAMPLE

Twelve infant patients, ranging in age from about 6 months to about 20 months, required invasive type therapy. These twelve infants were fitted experimentally with pediatric vests in accordance with the present invention. The infants, while wearing the vests, were examined for a total of about 419 catheter days ranging from about 4 to about 60 days with an average of 35 days per infant. During the experimental use of the vests, not one infant lost an infused line while wearing the vest, as compared to the loss of four (4) infused lines which were bitten or pulled out by 4 different infant patients not wearing the vests in a one month time period prior to the experimental use of the vests.

The present invention may, of course, be carried out in other specific ways than those herein set forth without departing from the spirit and essential characters of the present invention. For instance, although the garment or vest is described with crotch portions, it can be easily modified to include a bunting portion and still comply with the objectives of the present invention. Still further, the garment or vest of the present invention can be made with a single front panel and two back panels adapted to be joined together at the back of the patient without departing from the spirit of this invention. Still further, although this invention is described primarily for use with infants, it should be understood that the garment or vest of this invention can be sized for and utilized by, for example, toddlers, small children, teenagers and adults also undergoing invasive therapy. Even further, while side openings 21 are described as being located adjacent to the slit edges 20, it should be appreciated that the garment can be constructed with one or more openings at the same or different locations for enabling portions of the connected lines located beneath the garment to exit from therebeneath. The present embodiments are, therefore, to be considered in all respects as illustrative and not restrictive and any changes coming within the meaning and equivalency range of the appended claims are to be embraced therein.

What is claimed is:

1. A garment for shielding from a patient's head and limbs a line connected to the patient during invasive therapy, said garment comprising
   a vest portion having front and back panels, arm openings and a neckline edge wherein the front and back panels have interior and exterior sides, said vest portion further having a length to extend from the neckline edge down to about the waist of the patient and exiting means for permitting a portion of the connected line to exit from therebeneath when said garment is in position on the patient, and
   anchoring means secured to said vest portion for anchoring a portion of the connected line for shielding the connected line from the patient's head and limbs during the invasive therapy.

2. A garment of claim 1 wherein said anchoring means is positioned on the exterior side of the back panel for anchoring a portion of the connected line which has exited from beneath said positioned garment through the aperture for shielding the connected line from the patient's head and limbs during the invasive therapy.

3. A garment of claim 1 wherein said anchoring means is positioned on the interior side of the front panel for anchoring a portion of the connected line located beneath said positioned garment during the invasive therapy.

4. A garment of claim 3 wherein said anchoring means comprises a fabric material sewn to the interior side of the front panel.

5. A garment of claim 1 wherein the neckline edge is positioned immediately adjacent to the patient's neck adapted for further shielding a portion of the connected line located beneath said positioned garment during the invasive therapy.

6. A garment of claim 1 wherein said exiting means is an aperature.

7. A garment of claim 6 further including means for opening and closing the aperture.

8. A garment of claim 1 further including a crotch portion having leg-openings and adjusting means for adjusting said crotch portion to accommodate the patient's height, said crotch portion having a length to extend from about the patient's waist down to at least the crotch of the patient for fitting said crotch portion about the patient's crotch and legs when said garment is in position on the patient.

9. A garment of claim 1 wherein the front panel comprises two oppositely opposed panels for attaching at the front of the patient in an overlapping position.

10. A garment of claim 1 wherein the back panel comprises two oppositely opposed panels for attaching at the back of the patient in an overlapping position.

11. A garment of claim 1 wherein said anchoring means comprises a fastener component and a corresponding cooperative fastener component for anchoring a portion of the connected line.

12. A garment of claim 1 further including a bunting portion which has a length to extend from about the patient's waist down to and around the patient's legs and feet for covering the patient's crotch, legs and feet when said garment is in position on the patient.

13. A garment for shielding from a patient's head and limbs a line connected to the patient during invasive therapy, said garment comprising
   a vest portion having a back panel and a pair of oppositely opposed front panels for attaching at the front of the patient in an overlapping position wherein the back and front panels have interior and exterior sides, the front panels include a neck encircling edge, shoulder edges and side edges and arm hole edges extending between the shoulder edges and side edges and having an aperture for permitting a portion of the connected line to exit from beneath said garment when said garment is positioned on the patient during the invasive therapy, the back panel being secured along the shoulder and side edges of the front panels and having an opposed neck encircling edge to form an opening for the head and opposing arm hole edges to form openings for the arms of the patient, the back and front panels having a length to extend from the shoulder edges down to about the waist of the patient,
   means for opening and closing the aperture,
   anchoring means secured to said vest portion for anchoring portions of the connected line, and
   a crotch portion having a back tail and two oppositely opposed front tails for attaching to one another at the crotch of the patient, the front and back tails having waist edges and tail edges and leg hole edges extending between the waist and tail edges and a length to extend from about the patient's waist down to at least the crotch of the patient whereby, when said garment is positioned on the patient during invasive therapy, said garment conforms to the torso of the patient without restraining the patient's head and limbs while shielding the connected line from the patient's head and limbs.

14. A garment of claim 13 wherein said anchoring means is positioned on the exterior side of the back panel for anchoring portions of the connected line which have exited through the aperture from beneath said positioned garment during the invasive therapy.

15. A garment of claim 13 wherein said anchoring means is located on the interior side of at least one front panel for anchoring a portion of the connected line located beneath said positioned garment during invasive therapy.

16. A garment of claim 13 further including means for opening and closing the aperture.

17. A garment for shielding from a patient's head and limbs a line connected to the patient during invasive therapy, said garment comprising
   a vest portion having a front panel and a pair of oppositely opposed back panels for attaching at the back of the patient in an overlapping position wherein the back and front panels have interior and exterior sides, the front panel includes a neck encircling edge, shoulder edges and side edges and arm hole edges extending between the shoulder edges and side edges and having an aperature for permitting a portion of the connected line to exit from beneath said garment when said garment is positioned on the patient during the invasive therapy, the back panels being secured along the shoulder and side edges of the front panel and having opposed neck encircling edges to form an opening for the head and opposing arm hole edges to form openings for the arms of the patient, the front and back panels having a length to extend from the shoulder edges down to about the waist of the patient, means for opening and closing the aperture, anchoring means secured to said vest portion for anchoring portions of the connected line, and a crotch portion having a front tail and two oppositely opposed back tails for attaching to one another at the crotch of the patient, the front and back tails having waist edges and tail edges and leg hole edges extending between the waist and tail edges a a length to extend from about the patient's waist down to at least the crotch of the patient whereby, when said garment is positioned on the patient during invasive therapy, said garment conforms to the torso of the patient without restraining the patient's head and limbs while shielding the connected line from the patient's head and limbs.

18. A garment of claim 17 wherein said anchoring means is positioned on an exterior side of at least one back panel for anchoring portions of the connected line which have exited through the aperture from beneath said positioned garment during the invasive therapy.

19. A garment of claim 17 wherein said anchoring means is located on the interior side of the front panel for anchoring a portion of the connected line lcoated beneath said positioned garment during invasive therapy.

20. A garment of claim 17 further including means for opening and closing the aperture.

* * * * *